United States Patent [19]
Freeman et al.

[11] Patent Number: 5,725,506
[45] Date of Patent: Mar. 10, 1998

[54] DEVICE FOR PARACENTESIS AND THORACENTESIS

[75] Inventors: Shirley K. Freeman, Pine; David Skinkle; Bonnie B. Vivian, both of Evergreen, all of Colo.

[73] Assignee: Denver Biomaterials, Inc., Evergreen, Colo.

[21] Appl. No.: 583,813

[22] Filed: Jan. 5, 1996

[51] Int. Cl.⁶ ..................................................... A61M 5/178
[52] U.S. Cl. ........................... 604/169; 604/247; 128/766
[58] Field of Search ..................................... 604/164, 165, 604/167, 169, 170, 247, 158; 128/753, 754, 752, 766

[56] References Cited

U.S. PATENT DOCUMENTS

| | | | |
|---|---|---|---|
| 2,623,521 | 12/1952 | Shaw | 604/170 |
| 5,334,159 | 8/1994 | Turkel | 604/158 |
| 5,356,394 | 10/1994 | Farley | 604/256 |
| 5,370,623 | 12/1994 | Kreamer | 604/165 |
| 5,403,284 | 4/1995 | Gross | 604/167 |

*Primary Examiner*—Sam Rimell
*Assistant Examiner*—Luke Yeh
*Attorney, Agent, or Firm*—Davis, Graham & Stubbs, LLP

[57] ABSTRACT

A method and apparatus for removing fluid from the body of a patient, such as in paracentesis and thoracentesis, is provided. Fluid may be withdrawn via a needle assembly including a sharp introducing needle and a retractile blunt needle. The needle assembly may be withdrawn after the introduction of a drainage catheter, and a valve with multiple sealing points prevents body fluids from leaking from the device through the needle space and prevents communication between the atmosphere and the patient through the needle space. A second drainage port may be used after the needle is withdrawn.

19 Claims, 3 Drawing Sheets

DEVICE FOR PARACENTESIS AND THORACENTESIS

FIELD OF THE INVENTION

The present invention relates to the field of medical devices and, in particular, to a device useful for paracentesis and thoracentesis.

BACKGROUND OF THE INVENTION

Body fluids may need to be withdrawn from a patient in the course of medical treatment. Two common medical procedures requiring fluid removal are thoracentesis and paracentesis.

In paracentesis, peritoneal fluid is aspirated from the abdomen. Typical patients have tense ascites resulting from liver disease and portal hypertension, which may cause discomfort, respiratory distress, and the formation and rupture of umbilical hernias. Paracentesis has been observed to provide quick and effective relief with few adverse side effects. Other treatment options, such as the use of diuretics, are available, but may not provide as effective relief as paracentesis. Additionally, many patients with ascites have renal impairment and cannot use the high doses of diuretics necessary to effectively treat the ascites. See "Large-Volume Paracentesis in Nonedematous Patients with Tense-Ascites: Its Effect on Intravascular Volume," Pinto et al., *Hepatology*, vol.8, no. 2, pp. 207–210, 1988. Relatively large volumes of fluid, such as five liters, may be withdrawn from a patient during one paracentesis procedure.

Many existing devices are capable of performing paracentesis. At its simplest, a paracentesis device need only include a hollow needle with one end inserted into the patient and the other end attached to a negative pressure device such as a syringe or vacuum bottle. However, more specialized devices have been developed to allow safer, more comfortable, and more sanitary paracentesis. These devices may allow for body fluid to be dispensed into at least two containers, so that one container may be filled with fluid for diagnostic purposes and the other container may be filled with waste fluid. Another development has been the use of Kuss or Verres type needle assemblies where a blunt drainage needle is attached to a retractile sharp introducer needle. This reduces the likelihood of the sharp needle damaging internal tissue during paracentesis. A further development is to drain body fluid through a blunt tipped catheter introduced by a sharp introducing needle, which allows the sharp needle to be removed from the patient after a relatively quick introduction process and avoids the prolonged presence of a sharp needle in the body of the patient.

Problems may arise when drainage is diverted from one container to another if the drainage system is not airtight. Air could contaminate a sample or enter the body of the patient and cause injury. Known devices that are meant to be airtight have tubes and multiple containers attached to the devices which make the devices cumbersome and somewhat difficult to insert into the patient. Also, known devices require manipulation of a manual valve such as a stopcock to work effectively. If the stopcock is not set at the proper setting, the device may admit air into the patient or otherwise malfunction. Problems also may arise in devices which allow a needle to be withdrawn. Air must be prevented from entering the patient when the fluid is withdrawn. Also, body fluid must be prevented from leaking out of the device through the space formerly occupied by the needle.

Thoracentesis is a procedure similar to paracentesis except that effusion fluid is withdrawn from the pleural region instead of the abdomen. Normally, the pleural space contains approximately 5 to 20 ml of fluid. The fluid is the result of the hydrostatic-onctotic pressure of the capillaries of the parietal pleura. The turnover of the fluid in the pleural space is normally quite rapid so that 5 to 10 liters of fluid move through the pleural space each day. A disruption in the balance between the movement of fluid into the pleural space and the movement of fluid out of the pleural space may produce excessive fluid accumulation in the pleural space. Pleural effusion is particularly common in patients with disseminated breast cancer, lung cancer or lymphatic cancer and patients with congestive heart failure, but also occurs in patients with many other forms of malignancy.

Pleural effusion may cause dyspnea, coughing, and chest pain which diminish a patient's quality of life. Although pleural effusion typically occurs towards the end of terminal malignancies such as breast cancer, it occurs earlier in other diseases. Therefore, relieving the clinical manifestations of pleural effusion is of real and extended advantage to the patient. For example, non-breast cancer patients with pleural effusion have been known to survive for years. See "Pleural Effusion in Cancer Patients," Izbicki et al., *Cancer*, October 1975, p. 1511.

There are several treatments for pleural effusion. If the patient is asymptomatic and the effusion is known to be malignant or paramalignant, no treatment may be required. Pluerectomy and pleural abrasion is generally effective in obliterating the pleural space, thus controlling the malignant pleural effusion. However, pluerectomy is a major surgical procedure associated with substantial morbidity and some mortality. Chemotherapy is generally disappointing; however, it may produce good responses for patients with lymphoma, breast cancer, or small cell carcinoma. Another approach is to surgically implant a chest tube. However, such a tube is painful to the patient, both when it is inserted and during the time that it remains in the pleural space. Improvements on the traditional chest tube are described in U.S. patent application Ser. No. 08/251,692, commonly owned with the present application.

Despite other treatment options, thoracentesis remains the most common approach to removing pleural fluid. However, thoracentesis poses the danger of causing pneumothorax, a collapsed lung. Pneumothorax can be caused directly by puncturing a lung with a needle or catheter tip or indirectly by allowing air to enter the pleural space. Normally, the pleural space is at negative pressure relative to the atmosphere, which helps keep the lungs expanded. If the atmosphere is allowed to communicate with the pleural space, the pleural space may no longer be at negative pressure and pneumothorax may result.

Thoracentesis devices have been developed to reduce the risk of pneumothorax and other similar problems that may result from the procedure. In general, these devices incorporate similar protections as do paracentesis devices. For example, U.S. Pat. No. 4,447,235 by Clarke discloses a thoracentesis device with a catheter introduced by a removable needle, with a valve that closes upon removal of the needle. The purpose of the valve is to prevent air from entering the body of the patient. U.S. Pat. Nos. 4,784,156, 4,832,044, 4,840,184, and 4,844,087 by Garg disclose similar devices with a manual valve that may be closed after withdrawal of the needle. However, none of the previous devices allow for truly fail safe operation, as various valves must be properly set by the operator when changing from one drain port to another or when withdrawing the introducing needle from the patient. Also, care must be taken to avoid accidental withdrawal of the introducing needle, as in the disclosed devices the needle is not firmly attached to the remainder of the device. Further, the disclosed valves that allow for catheter drainage after removal of an introducing needle rely on a single contact point. Due to the possibly dire consequences of a valve failure, such valves may not produce acceptably safe thoracentesis.

A Verres type needle assembly that may be used for thoracentesis is disclosed in U.S. Pat. No. 5,334,159 by Turkel. While this reduces the risk of pneumothorax due to lung puncture, the Turkel device does not improve the safety of thoracentesis when the introducing needle is withdrawn or solve the problems associated with multiple drainage ports. Thus there is a need for a safer and more reliable device that may be used for paracentesis and thoracentesis.

SUMMARY OF THE INVENTION

The present device for fluid removal from the body of a patient is characterized by the incorporation of several features to reduce the likelihood of damage to a patient during the procedure and to facilitate the fluid removal process. The primary components of the drainage device are a Verres type needle assembly partially surrounded by a catheter, a housing through which the needle assembly and catheter pass, and a detachable handle to which the needle assembly is attached at its end opposite the end to be inserted into the patient.

The Verres type introducing needle assembly includes a sharp outer needle and a blunt retractile inner needle. The inner needle is biased so that it projects ahead of the outer needle in the absence of an axial force on the inner needle. An axial force on the inner needle causes it to retract into the outer needle so that the sharp tip of the outer needle is exposed. Thus, pressing the device against the skin and dense outer tissue of a patient causes the sharp needle to become exposed and allows the needle assembly to cut through the skin and dense outer tissue and enter the body of the patient. When the needle assembly tip enters the fluid pool to be drained, however, there is no axial force on the inner needle and it extends from the outer needle. Once the Verres needle assembly is in the fluid pool, the sharp needle is buffered by the blunt needle and is less likely to cut into a patient's sensitive inner tissue. The device operator is made aware of whether the inner needle is projected ahead of the outer needle or recessed into the outer needle by means of an indicator that attaches to the end of the inner needle opposite the end that is inserted into the patient, and thus the operator may determine whether the needle tip has entered the fluid pool.

Fluid may be withdrawn through the Verres needle assembly through a drainage port on the device fitted with a Luer lock by applying negative pressure at the Luer lock. After the operator has withdrawn a quantity of fluid through the Verres needle assembly and is satisfied that the device is properly positioned, the Verres needle assembly may be withdrawn and further fluid may be withdrawn through the catheter. This allows for safer fluid withdrawal since the sharp tipped inner needle is removed from the body of the patient and for faster fluid withdrawal since the catheter has a larger diameter than the Verres needle assembly. The needle is withdrawn from the device by detaching the handle to which the Verres needle assembly is attached from the remainder of the device. A locking feature joining the handle to the housing insures that the Verres needle assembly will not be inadvertently withdrawn.

Withdrawing an introducing needle from a fluid removal device is a critical stage in the fluid removal process because of the possibility of air entering the patient through the space formerly occupied by the needle. Also, it is possible that fluid may leak out of the device through the same space. The present invention prevents both of these potential hazards by means of an automatic sealing valve that seals the space through which the needle assembly passes. In a preferred embodiment, the sealing valve blocks the needle space at two points, adding redundancy to the seal. The seal is formed by two plungers separated by a compressed spring. Each plunger has a stem attached to a conical head, and the stem of one plunger fits into the stem of the other plunger with the conical heads of the plungers pointing in opposite directions. The plungers fit into a cavity in the housing so that the conical head of one plunger fits against a ramp leading to a restriction in the cross section of the cavity and the other plunger fits against another ramp leading to a second restriction in the cross section of the cavity. The spring between the plungers attempts to force the plungers apart by sliding the plungers up their respective ramps. However, the Verres needle assembly is initially placed directly above the plungers and in contact with them, so that the plungers cannot separate and the spring remains compressed. When the needle is withdrawn, the plungers separate; each plunger slides up its ramp until the conical heads of the plungers fit into the restricted cross sections of the housing. The spring disposed between the plungers is sufficiently long to continue to apply a separating force to the plungers once they are seated in the restricted cross sections. This maintains pressure between the plungers and the housing to form a secure seal.

Besides adding redundancy to the seal, the plunger design allows the spring which creates the sealing force to be placed with its axis aligned with the axis of the device. This allows for a slimmer device profile than would be possible if the spring were placed with its axis transverse to the device axis, as is seen in the prior art.

After the needle is withdrawn, fluid may be withdrawn through the catheter through a second drainage port fitted with a Luer lock, by attaching a negative pressure device to the drainage port. The second port is blocked by the needle until the needle is removed from the device. A sealing valve, preferably an elastomeric slit disc valve, prevents the flow of air or fluid through the second port until a male Luer fitting is attached, coupled to a negative pressure device. This sealing valve allows the negative pressure device to be attached to the second drainage port at any stage of the fluid withdrawal process. This is advantageous as it may be easier to first insert the device into the patient without any attachments to the second drainage port, so that the device is more maneuverable. The valve also requires no manual adjustment.

The device may be inexpensively manufactured and is designed to be disposed of after one use. The Verres needle assembly is preferably made of metal such as stainless steel. The catheter may be made of metal or plastic or other suitable material, plastic being somewhat softer than metal and hence providing additional safety for thoracentesis. The device housing and handle are made of rigid plastic, such as ABS plastic. The device housing may be made of several parts which are joined together after the seals are placed in the housing. The second drainage port seal and the plunger seal that occupies the needle space are elastomeric to provide compressive sealing.

DETAILED DISCLOSURE OF THE INVENTION

Figure 1:
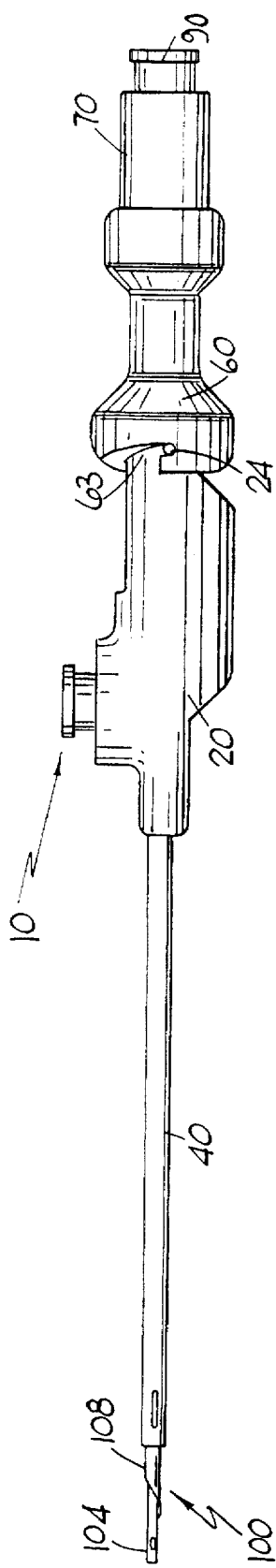
FIG. 1 shows a side view of an embodiment of the present invention.
Figure 2:
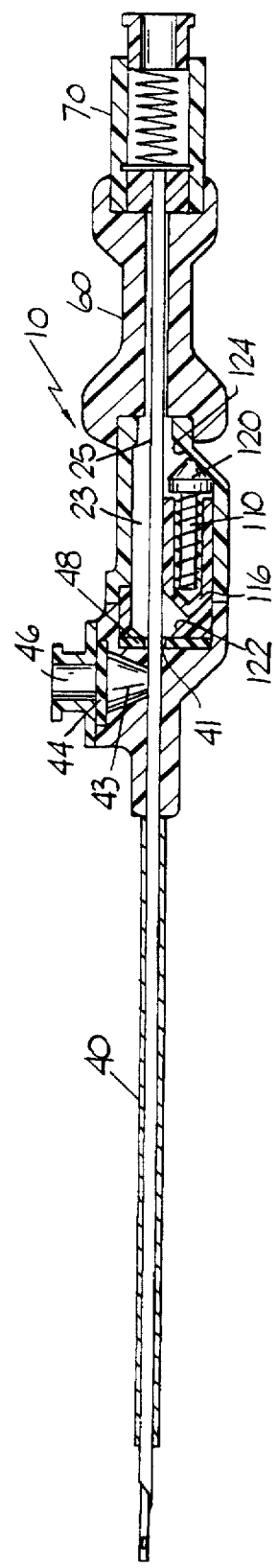
FIG. 2 shows a side sectional view of an embodiment of the present invention.
Figure 3:
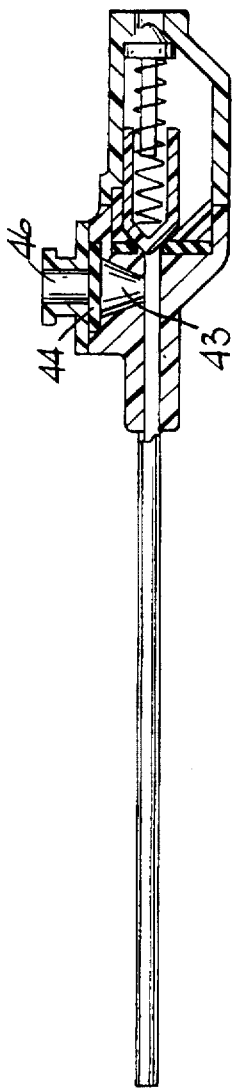
FIG. 3 shows the view of FIG. 2 after the introducing needle assembly has been withdrawn from the device.

As best seen in FIGS. 1 and 2, a paracentesis and thoracentesis device 10 includes a housing 20 with a drainage cannula 40 extending from the distal end of the housing 20. A transverse opening 43 near the proximal end of the cannula 40 leads through a valve 44 to a transverse Luer lock 46 in the housing 20. The proximal end of the cannula 40 joins an interior cavity 23 in the housing 20 at a cannula opening 41. The cross section of the interior cavity 23 is larger than the that of the cannula 40; the interior cavity 23 extends proximally until its cross sectional diameter is reduced at its proximal end to form a proximal restriction 25. An opaque detachable handle 60 attaches concentrically around the proximal end of the housing 20, and a transparent indicator housing 70 is situated so that a distal portion fits concentrically into the handle and a proximal portion extends proximal to the handle 60. The proximal end of the indicator housing 70 houses a proximal Luer lock 90. Both the handle 60 and the indicator 70 are hollow so that the proximal restriction 25 continues from the interior cavity 23 through a hole through the handle 60 and the indicator 70 to a proximal Luer lock 90.

Figure 4:
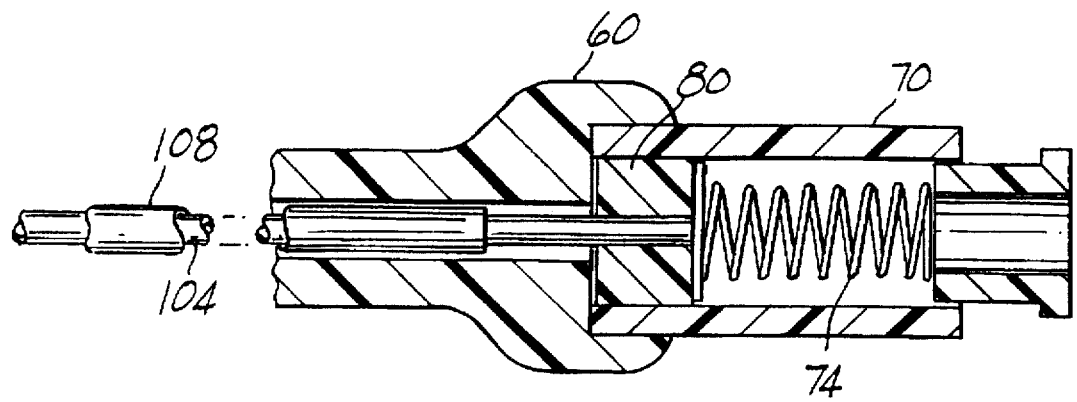
FIG. 4 shows a detailed sectional view of the needle position indicator of the present invention when the inner needle protrudes from the sharp outer needle.
Figure 4A:
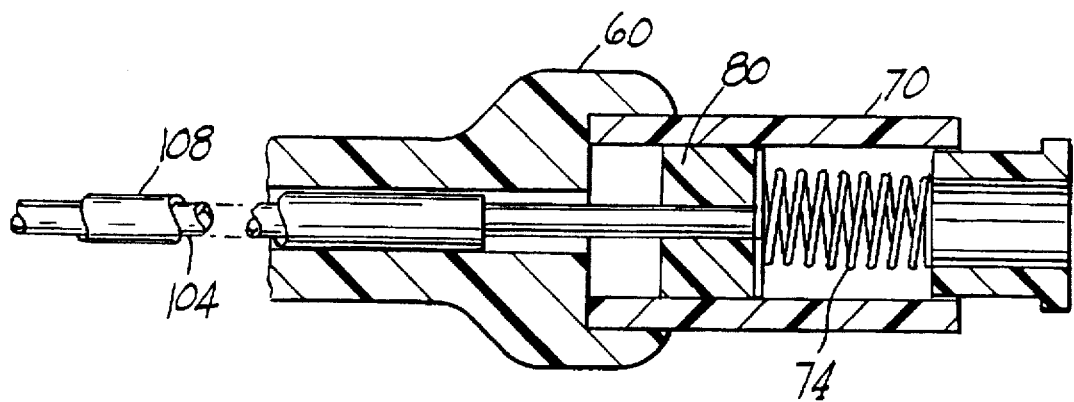
FIG. 4A shows the view of FIG. 4 when the inner needle is recessed into the outer needle, exposing the sharp outer needle.

A Verres needle assembly 100 attaches to the handle 60 and extends through the proximal restriction 25, the interior cavity 23, and the cannula 40 and terminates distal to the cannula 40. The Verres needle assembly 100 includes an inner needle 104 with a blunt distal end and an outer needle 108 with a sharp distal end that fits concentrically around the inner needle 104. The outer needle 108 is firmly attached to the handle 60, such as by a gluing the two together. The inner needle 104 extends proximally to the outer needle 108. The inner needle 104 and outer needle 108 are slidably attached to each other, with the inner needle 104 biased by an indicator spring 74 so that, in the absence of a force to compress the spring 74, the inner needle projects distal to the outer needle 108 (see FIG. 4). When force is applied to the inner needle 104 in the proximal direction, the spring 74 compresses and the inner needle 104 recesses into the outer needle 108 (see FIG. 4A). The biasing spring 74 is located on the interior surface of the indicator housing 70, with the distal end of the spring 74 terminated to the proximal end of inner needle 104. Both the catheter 40 and the inner needle 104 contain fenestrations in their sidewalls near their distal ends to facilitate fluid drainage.

An indicator 80 is fixed to the proximal end of the inner needle 104. The indicator 80 may be of any material, such as a colored piece of plastic, that is visible to the human eye. In a preferred embodiment, the indicator 80 is a colored plastic cylinder that fits concentrically around the inner needle 104. The dimensions of the inner needle 104 and the indicator 80 are such that when the inner needle 104 protrudes from the outer needle 108, neither the proximal end of the inner needle 104 nor the indicator 80 extend beyond the handle 60 (see FIG. 4). At this point, the indicator is not visible to the operator of the device 10. However, when the inner needle 104 recesses into the outer needle 108, the indicator 80 slides proximally along with the inner needle 104 so that the indicator 80 becomes visible through the transparent indicator housing 70 (see FIG. 4A).

In its initial position, the handle 60, and hence the Verres needle assembly 100, is fixed in relation to the housing 20. A tab 24 protrudes from the housing 20 and fits into a tangential slot 63 on the handle 60 to fix the handle 60 in an initial position. The handle 60 may be rotated around the housing 20 so that the tab 24 is removed from the slot 63. Once the tab 24 is removed from the slot 63, the handle 60 may withdrawn proximally from the housing 20. As the Verres needle assembly 100 is attached to the handle 60, the Verres needle assembly 100 may be proximally removed from the housing 20 by sliding the handle 60 proximally from the housing 20.

Figure 5:
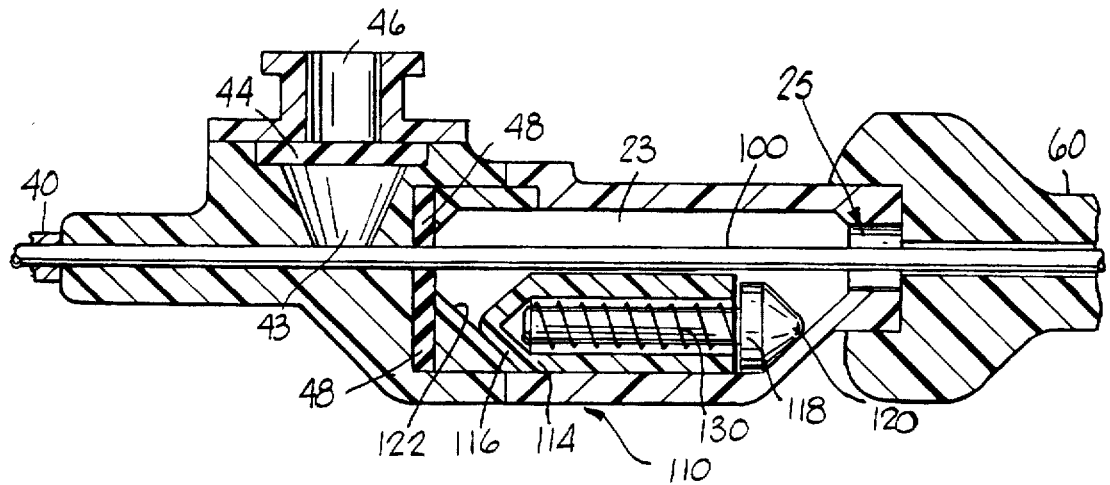
FIG. 5 shows a detailed sectional view of the sealing plunger of the present invention before the introducing needle has been withdrawn.

The interior cavity 23 is shaped to hold a sealing plug 110 radially between the surface of the interior cavity 23 and the Verres needle assembly 100 (see FIG. 5). The sealing plug 110 includes two plungers 114 and 118, each having a conical head and a cylindrical stem. The conical head 116 of plunger 114 is oriented in the distal direction so its tapered section points to the distal end of the cannula 40. The conical head 120 of plunger 118 is oriented in the proximal direction so that it faces the proximal restriction 25. The conical head 116 of plunger 114 fits against a ramp 122 formed into the interior cavity 23 that slopes from the relatively wide center portion of the interior cavity 23 towards the more narrow cannula opening 41. Likewise, the conical head 120 of plunger 118 fits against a ramp 124 formed into the interior cavity 23 that slopes from the interior cavity 23 towards the more narrow proximal restriction 25.

Figure 5A:
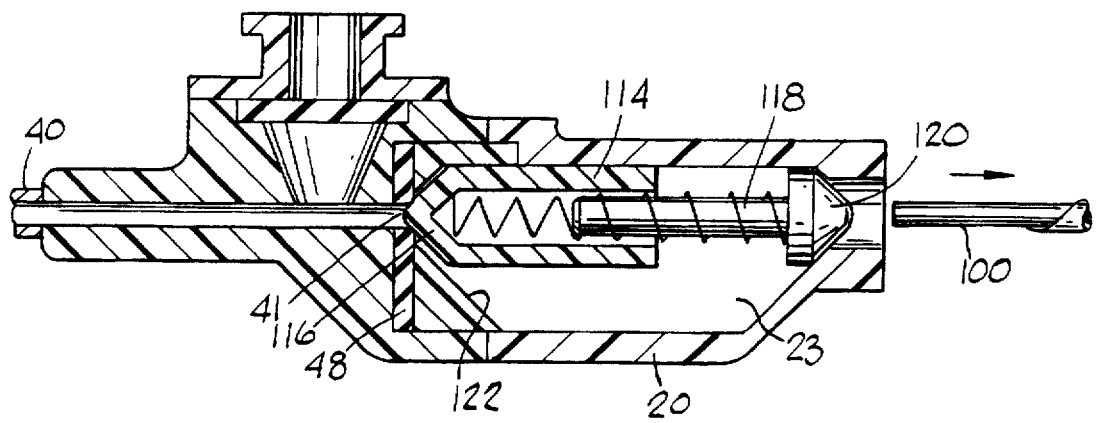
FIG. 5A shows a detailed sectional view of the sealing plunger after the introducing needle has been withdrawn.

The stem of plunger 114 is a hollow cylinder that houses the cylindrical stem of plunger 118. A plunger biasing spring 130 fits in an annular space between the nested stems of plungers 114 and 118. When the spring 130 is fully compressed, the plungers fit together so that the proximal end of the stem of plunger 114 abuts the base of the conical head 120 of plunger 118. The spring 130 attempts to decompress and exerts a force to push plungers 114 and 118 away from each other. However, so long as the Verres needle assembly 100 is in contact with the plungers 114 and 118, they cannot separate from each other as they are bounded by the ramps 122 and 124 and the Verres needle assembly 100, and the spring 130 remains compressed. When the Verres needle assembly 100 is removed, however, the spring 130 may decompress and slide the plungers 114 and 118 away from each other (see FIG. 5A). Plunger 114 will slide up ramp 122 and plunger 118 will simultaneously slide up ramp 124. The length of the spring 130 and the stems of the plungers 114 and 118 is sufficient to drive the conical head 116 of plunger 114 into the cannula opening 41 and the conical head 120 of the plunger 118 into the proximal restriction 25, thus sealing the interior cavity 23 from both the cannula opening 41 and the proximal restriction 25.

The operation of the device 10 to withdraw fluid from a patient may now be understood. To perform thoracentesis, for example, the Verres needle assembly 100 is introduced into the pleural space of a patient. Before the Verres needle assembly 100 is positioned against skin of a patient, the inner needle 104 projects distal to the outer needle 108. As the device 10 is pressed against the skin, pressure on the inner needle 104 causes the indicator spring 74 to compress and the inner needle 104 recesses into the outer needle 108 until the outer needle 108 is adjacent the skin of the patient. Further pressure on the device 10 causes the outer needle 108 to puncture the skin and dense outer tissue of the patient and to enter the patient's pleural cavity. While the outer needle 108 is cutting through tissue, axial pressure on the distal tip of the inner needle 104 keeps the inner needle recessed into the outer needle 108. Once the Verres needle assembly 100 enters the pleural cavity, the pressure on the distal tip of the Verres needle assembly 100 is removed and the indicator spring 74 decompresses and projects the inner needle 104 distal to the outer needle 108. The operator of the device 10 is made aware of the point where the Verres needle assembly 100 has entered the pleural cavity by the position of the indicator 80; the indicator 80 will not be visible through the indicator housing 70 when the Verres needle assembly 100 is in the patient's pleural cavity.

It should be apparent that the use of a Verres needle assembly 100 serves to protect the patient's sensitive inner tissue, particularly the lungs, from inadvertent puncture by the sharp outer needle 108. Once the operator of the device 10 detects that the Verres needle assembly 100 is in the pleural cavity, the operator may stop the distal motion of the Verres needle assembly 100. Further inadvertent distal motion, by either the device 10 operator or the patient, is relatively harmless until the blunt inner needle 104 contacts sensitive tissue and further distal motion causes the inner needle 104 to fully recess into the sharp outer needle 108. Harm to a patient may occur if the patient moves in the proximal direction as well as when the operator of the device 10 moves the device 10 in the distal direction. Such movement is a particular problem in thoracentesis, since a patient's lungs move proximally and distally as the patient inhales and exhales. So while the Verres needle assembly 100 affords some protection against pneumothorax or other tissue harm, it is by no means fail safe.

Fluid may be withdrawn through the Verres needle assembly 100 through the proximal Luer lock 90 attached to the indicator 70 by means of a negative pressure device (not shown), such as a syringe, attached to the proximal Luer lock 90. The negative pressure device may be attached to the Luer lock 90 before the device 10 is introduced into the body of the patient so that the no air enters the body of the patient through the device 10. Alternatively, an air-tight cap or plug (not shown) may be fitted over the Luer lock 90 to prevent air from being introduced into the patient. It is possible that body pressure and capillary action may cause body fluid to flow into the annular space separating the drainage cannula 40 and the outer needle 108. However, a sealing gasket 48 placed around the sharp needle 108 distal to the side drainage port 43 blocks the flow of fluid beyond the sealing gasket 48.

After the operator of the device 10 determines that the fluid is flowing properly and desires that more fluid be withdrawn from the patient, the drainage may be completed through the catheter 40 and the side drainage port 43 instead of through the Verres needle assembly 100 and the proximal Luer lock 90. The transition is initiated by the operator withdrawing the Verres needle assembly 100 from the patient while keeping the housing 20 fixed. This is accomplished by rotating the handle 60 so that the tab 24 on the housing 20 is no longer in the tangential slot 63 of the handle 60, then pulling the handle 60 in the proximal direction while maintaining the position of the housing 20. Body fluid may then flow directly through the drainage cannula 40. As the Verres needle 100 is withdrawn proximal to the sealing plunger 110, the sealing plunger 100 moves from its initial position bounded by the Verres needle assembly 100 to its second position, as explained above. The sealing plunger 110 blocks the interior cavity 23, so that no fluid may flow proximal to the sealing plunger 110 and no air may flow through the central cavity 23 into the catheter 40 from the interior cavity 23.

The advantages of the sealing plunger 110 may now be appreciated. The sealing plunger 110 blocks the interior cavity 23 at two locations (the cannula opening 41 and the proximal restriction 25), adding redundancy to the seal. Thus, if one of the plunger conical heads 118 or 122 should fail to make an adequate seal, flow through the device 10 will still be blocked by the remaining plunger. The integrity of the seal is important for at least two reasons. First, an inadequate seal may allow body fluid to flow proximal to the proximal restriction 25. With the handle 60 withdrawn from the housing, the fluid would flow outside the body of the housing 20 and thus leak from the device 10. As well as being unsanitary, the fluid may pay pose a risk of infection to those in the vicinity of the device 10. A second danger arises when the device 10 is used for thoracentesis. The distal end of the device 10 is placed into the pleural cavity, which must be kept at negative pressure to avoid the risk of a lung collapsing (i.e., pneumothorax). It is imperative that the pressure of the atmosphere not be allowed to communicate with the patient's pleural space. If the plunger 110 seal was defective, then air may pass through the proximal restriction 25 of the device 10 and the drainage catheter 40 into the pleural opening, causing pneumothorax. The two point plunger seal 110 improves the safety of the device 10 by adding redundancy.

A further advantage of the sealing plunger 110 design is that the spring force applied by the biasing spring 123 acts axially with respect to the interior chamber and space formerly occupied by the Verres needle assembly 100. This allows for a more compact design than a valve with a spring placed transverse to the space previously occupied by the introducing needle. With a spring such as spring 123, the length of the spring does not affect the radial extension of the spring away from the axis of the device 10. A transverse spring, however, must extend radially away from the former needle spring. A transverse spring of sufficient length to provide adequate sealing force may appreciably add to the cross sectional bulk of a fluid removal device, and hence interfere with its ease of operation.

After removal of the Verres needle assembly 100, drainage is accomplished directly through the drainage cannula 40 and the locking Luer fitting 46 of the right angle drain port 43. Removal of the Verres needle assembly 100 from the body of the patient is desirable to eliminate the possibility of the sharp outer needle 108 from severing tissue, particularly the lungs, of the patient. While the blunt inner needle 104 of the Verres needle assembly 100 reduces the danger posed by the sharp outer needle 108, additional safety is achieved by removing the Verres needle assembly 100 entirely from the patient. Also, the diameter of the drainage cannula 40 is greater than the diameter of the blunt needle 104 of the Verres needle assembly 100, so that fluid may be withdrawn more rapidly. The two drainage ports 46 and 90 also allow fluid to be collected into separate containers. This may be useful as the device 10 operator may wish to withdraw a diagnostic sample through the proximal Luer lock 90, and withdraw the remaining fluid through the side Luer lock 46 for disposal.

As with the proximal Luer lock 90, any negative pressure device and storage container with a Luer fitting may be attached to the right angle drain port 43. Further, the right angle drain port 43 provides an airtight seal until a device fitted with Luer lock is attached to the Luer lock 46 of the drain port. This is desirable as air entering the device 10 through the drain port 43 could then enter the body of the patient and produce pneumothorax, as explained above. In a preferred embodiment, the seal is accomplished an elastomeric slit disk valve 44. Prior art body fluid drainage devices are equipped with valves, such as stopcocks, which require the operator to manually adjust the valve when changing the fluid flow from one drainage channel to another. A manual stopcock may endanger the patient if it is inadvertently set to the wrong setting. For example, the operator could bump the stopcock setting so that the stopcock would allow the entry of air through the device into the body of the patient. A partial solution to that danger has been to terminate the stopcock openings with sealed components before the drainage device is inserted into a patient. However, a drainage device so equipped must be bulky and the operator must bear in mind the relative positions of the various components of the device, which may make insertion of the device difficult. In the present invention, the device 10 is preferably inserted with no attachment to the side drainage port 43. There is no danger of accidently opening the Luer lock 46 on the side drainage port 43, and no drainage container need be attached to the side drainage port until after the device 10 is inserted into the patient.

What is claimed is:

1. An apparatus useful for fluid withdrawal,
    a housing, the housing having a distal end and a proximal end and a chamber extending through the housing from the distal end to the proximal end;
    a catheter extending from the distal end of the housing;
    a needle assembly including at least one needle, the needle assembly removably extending through the housing chamber and the catheter;
    a chamber valve that may be opened or closed, the valve being disposed between the needle assembly and the chamber, and the valve having at least two sealing points, so that the valve is open when the needle assembly extends through the chamber and the valve is closed when the needle assembly is withdrawn from the housing, the valve preventing fluid and gaseous communication through the chamber when it is closed;
    a handle removably attached to the housing, the handle being connected to the needle assembly so that the needle assembly may be removed from the housing chamber by removing the handle form the housing; wherein the needle assembly comprises;
    an outer needle having a proximal end and a sharp distal end;
    an inner needle having a proximal end and a blunt distal end, the inner needle being slidably contained within the outer needle; and
    a biasing element engaged with the inner needle and the outer needle so that the distal end of the inner needle projects distal to the distal end of the outer needle when no force is applied to the distal end of the inner needle.

2. The apparatus of claim 1, wherein the housing has a fluid flow port in fluid communication with the housing chamber, the fluid flow port communicating with the chamber distal to the chamber valve.

3. The apparatus of claim 2, wherein the chamber valve includes a spring that applies sealing force to the chamber valve, and the spring applies force along the direction defined by the proximal and distal ends of the housing chamber.

4. The apparatus of claim 3, wherein the chamber valve further comprises:
    a first plunger including a plunger head and a stem extending from the plunger head,
    a second plunger including a second plunger head and a second stem extending away from the plunger head, the first plunger stem being hollow and being able to receive the second plunger stem; and
    a spring interposed between the first and second plunger heads.

5. The apparatus of claim 4, wherein the housing chamber has a recessed section receiving the first and second plungers, the recessed portion being connected to the remainder of the chamber at two ramp sections, the plungers being bounded by the recessed portion of the chamber and the outer needle, so that when the needle assembly is removed from the chamber, the spring will force the plungers to slide away from each other and up the ramp section into the part of the chamber formerly occupied by the needle, so that the plunger heads will seal the chamber.

6. The apparatus of claim 5, wherein the first and second plunger heads are conically shaped and made of elastomeric material.

7. The apparatus of claim 6, further comprising: an elastomeric gasket disposed within the chamber distal to the ramp sections, so that when the needle assembly is retracted from the handle and the plungers slide away from each other to seal the chamber, one of the plunger heads contacts a portion of the gasket.

8. The apparatus of claim 7, wherein the handle includes a Luer lock in fluid communication with needle assembly.

9. The apparatus of claim 8, wherein the fluid flow port is a Luer lock located distal to the elastomeric gasket.

10. The apparatus of claim 9, further comprising: a valve proximate the fluid flow port that prevents fluid and gas flow through the port when the valve is closed and allows fluid flow through the port when the valve is open.

11. The apparatus of claim 10, wherein the valve proximate the fluid flow port is an elastomeric slit disk sealing washer.

12. The apparatus of claim 11, further comprising: an indicator that indicates the position of the inner needle with respect to the outer needle, the indicator being attached to the inner needle and at least part of the indicator extending distal to the outer needle.

13. The apparatus of claim 12, wherein the handle may attach to the housing in a locked position, and the handle may not be withdrawn from the housing when the handle is in the locked position.

14. The apparatus of claim 13, wherein the handle is locked into the housing by a protrusion on the housing that may be fitted into a slot on the handle.

15. The apparatus of claim 13, wherein the handle is locked into the housing by a protrusion on the handle that may be fitted into a slot on the housing.

16. A method for fluid withdrawal, comprising:
    (a) inserting the distal end of a fluid withdrawal apparatus into a body of fluid, the fluid withdrawal apparatus including a housing with a chamber extending therethrough, a catheter extending distal to the housing, a handle attached to the proximal end of the housing, and a needle extending from beyond the distal end of the catheter through the catheter and housing, and attaching to the handle;
    (b) withdrawing fluid through the needle;
    (c) removing the needle from the housing by detaching the handle from the housing;

(d) sealing the proximal end of the housing so as to prevent fluid and gaseous communication therethrough, the sealing being accomplished at least two sealing points.

17. The method of claim 16, wherein step (d) is accomplished automatically after completion of step (c).

18. The method of claim 17, further comprising the steps of:

(e) attaching a fluid removal container to a fluid removal port in the housing; and (f) withdrawing fluid through the catheter and into the fluid removal container.

19. The method of claim 18, wherein step (e) is performed after step (c).

* * * * *